US00PP22611P2

(12) United States Plant Patent
Zwagerman

(10) Patent No.: US PP22,611 P2
(45) Date of Patent: Mar. 27, 2012

(54) *HOSTA* PLANT NAMED 'DANCING STARS'

(50) Latin Name: ***Hosta hybrida* (Tratt.)**
Varietal Denomination: Dancing Stars

(75) Inventor: Mary E. Zwagerman, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 12/925,902

(22) Filed: Nov. 2, 2010

(51) Int. Cl.
*A01H 5/00* (2006.01)

(52) U.S. Cl. ..... Plt./353

(58) Field of Classification Search ..... Plt./353
See application file for complete search history.

*Primary Examiner* — Susan McCormick Ewoldt

(57) ABSTRACT

A new and distinct cultivar of *Hosta* plant named 'Dancing Stars', characterized by thick substance leaves having creamy yellow to creamy white centers and a deep green margins, with lavender flowers held nicely above foliage on upright cream-colored scapes.

1 Drawing Sheet

Botanical classification: *Hosta hybrida* (Tratt.).
Variety denomination: 'Dancing Stars'.

BACKGROUND AND ORIGIN OF THE PLANT

The present invention relates to the new and distinct *hosta* plant, *Hosta* 'Dancing Stars' discovered by Mary Zwagerman in the summer of 2007 at a greenhouse in Zeeland, Mich. as a whole plant, uninduced somaclonal variation among a batch of *Hosta* 'Dancing in the Rain' U.S. Plant Pat. No. 15,977. *Hosta* 'Dancing Stars' has been asexually propagated by tissue culture at a nursery in Piaseczno, Poland and the resultant asexually propagated plants have remained stable and true to type in successive generations of asexual reproduction.

The most similar known *hosta* cultivars known to the applicant are: *Hosta* 'American Sweetheart' (not patented), *Hosta* 'Eskimo Pie' U.S. Plant Pat. No. 16,290, *Hosta* 'Dancing in the Rain' U.S. Plant Pat. No. 15,977, *Hosta* 'Loyalist' (not patented), *Hosta* 'Night before Christmas' (not patented) and *Hosta* 'Sea Thunder' (not patented). All of the above have whitish leaf centers and green to bluish-green leaf margins. *Hosta* 'American Sweetheart' has a lustrous leaf underside, longer leaves with a more sharply acute apex than the new plant. 'Dancing in the Rain' is not as thick substance in the leaf, the margin is not as wide, there is slightly less color separation between the margin and the center, and the growth rate is not as fast as the new plant. 'Eskimo Pie' has more rounded leaves with a bluer margin, more rugose leaf surface and the adaxial surface is more glaucous and retains this longer in the season. 'Loyalist' has a greener leaf margin with less blue than the new plant, and shorter flowering scape with fewer flowers. 'Night before Christmas' is a larger plant in habit and in individual leaf size, and the leaf has veins that are more impressed. 'Sea Thunder' has a lustrous leaf underside, narrower green margins and thinner leaf substance.

*Hosta* 'Dancing Stars' is unique from its parent sport, *Hosta* 'Dancing in the Rain', and all other *hosta* cultivars known to the inventor, in the following combined traits:

1. Leaves emerge glaucous on both surfaces.
2. Leaves emerge with blue-green margins and light yellow centers and develop into dark green margins with white centers by mid season.

3. Leaves with thick substance with white centers resistant to melting out in high temperatures.
4. Light lavender flowers on upright cream-colored scapes.

BRIEF DESCRIPTION OF THE DRAWINGS

The photograph of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED BOTANICAL DESCRIPTION

Figure 1:
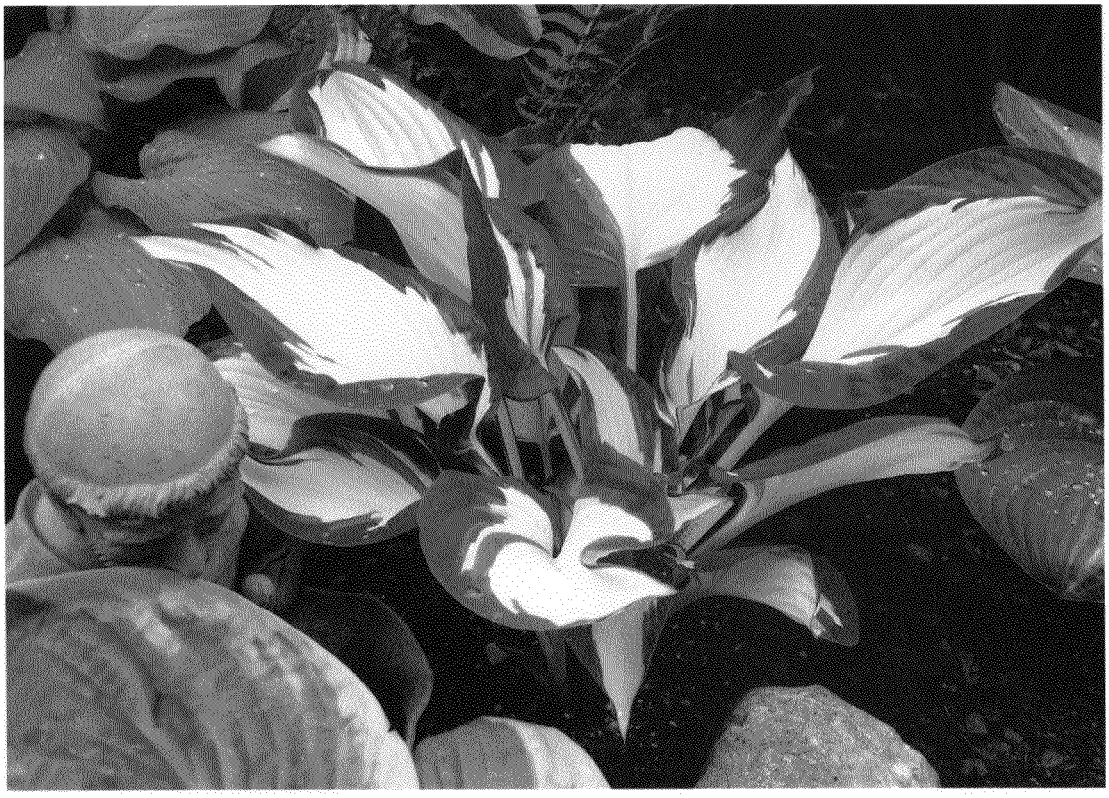
FIG. 1 shows of the plant at two-years old from about an angle of 45 degrees.

The following descriptions and color references are based on The Royal Horticultural Society Colour Chart (2001 edition) except where common dictionary terms are used. The new plant, *Hosta* 'Dancing Stars', has not been observed under all possible environments. The phenotype may vary slightly with different environmental conditions, such as temperature, light, fertility and moisture, but without any change in the genotype. The following observations and size descriptions are of a three-year old plant in a shade trail garden in Zeeland, Mich., USA with supplemental water and fertilizer, under 50% shade on cloudless days, day temperatures of 15° to 34° degrees C., and night temperatures of 8° to 20° C. during the growing season.

Botanical classification: *Hosta* hybrid cultivar 'Dancing Stars'.

Parentage: Naturally-occurring uninduced somaclonal variation of *Hosta* 'Dancing in the Rain' U.S. Plant Pat. No. 15,977.

Propagation: Method by tissue culture and division; time to initiate roots from both division and tissue culture three to four weeks from cutting.

Rooting habit: Normal, fleshy, to 3 mm thick, lightly branched.

Plant habit: Herbaceous, densely rhizomatous perennial, radially symmetrical with radical leaves upright to slightly arching through flowering period, more horizontal late in the season and in maturity.

Crop time: Under normal summer greenhouse growing conditions about 15 weeks to finish in a one-liter container; plant vigor is very good.

Plant size: At flowering is 40 to 60 cm tall and 60 to 90 cm wide.

Foliage description:

*Shape and size.*—Ovate to broadly ovate leaf blades, with sharply acute apex when mature and cordate base, slightly glaucous above becoming shiny, heavily glaucous below throughout growing season.

*Leaf blades.*—20 to 26 cm long and 12 to 18 cm wide.

*Color.*—Adaxial (upper) margin surface is a deep green closest to RHS 136A with a slight glaucous bloom in early summer and by mid to late season becoming lustrous, the center is between RHS 2B and RHS 2C in early summer and lightens to lighter than RHS 4D later in season; the intermediate sections between the margin and center include RHS N144A and RHS N138D; as a young plant, and especially in high heat, the leaf centers may occasionally become more green in a variable fogging or frosting manner from a light green of closest RHS 138C to a darker green closest RHS 136B. Abaxial margin surface begins the season closest to RHS 136B and develops to closest to RHS N138A with a glaucous surface that lasts all season; and the center is closest to RHS 2B early in the summer and lightens slightly to between RHS 4C and RHS 2C; the intermediate colors consist mainly of RHS N138D.

*Veins.*—Parallel slightly impressed on top and protruding on bottom; 8 to 9 pairs on each side of the main vein increasing with more maturity.

*Vein color.*—Same color as surrounding tissue on both surfaces; center vein abaxial side develops into RHS 144D in the proximal two thirds with the distal one third becoming RHS 2C; center vein on adaxial surface same as surrounding tissue.

*Leaf blade margins.*—Entire, the creamy yellow variegation pattern on the edge varies in different regions of the leaf and with different leaf maturities from 15 to 28 mm wide.

*Petioles.*—26 to 32 cm long and 9 to 11 mm wide; adaxial center color between RHS 1B and RHS 1C, abaxial center color variable — both colors RHS 10D and RHS 146D; margins between RHS 136A and RHS 137A on both top and bottom with a slight glaucous surface.

Flower description:

*Buds.*—Two days prior to opening the buds are violet RHS 85D and RHS 85A, 6 to 7 cm long, up to 1.5 cm wide.

*Flowers.*—Funnelform, 16 to 35 per scape, 4 to 6 cm wide and 6 to 8 cm long, (distal flowers being smaller); no detectable fragrance; persists for a normal period, up to two days, and the scapes remain effective from early July to late July.

*Tepals.*—Arranged in two layers of three, fused at proximal one half, with slightly recurved (opening beyond flat faced) acute apex; approximately 7 cm long and 1.2 cm wide, the inner three with clear 1 to 2 mm margin.

*Tepal color.*—Base color in center of nearest RHS 69D and violet stripes of RHS 84B; base of the tepals is between RHS 75B and 76B.

*Bract.*—Subtending each one to two flowers; lowest bract 5 cm long and 2 cm wide, decreasing to 10 mm long and 5 mm wide.

*Bract color.*—Closest to RHS 137A in the margin adaxial surface, center adaxial surface contains portions ranging from RHS 10C to RHS 155D; the abaxial center between RHS 10B and RHS 10D, and the margin closest to RHS 138A.

*Peduncle.*—Erect to slightly arching, up to 40 cm long and 0.8 cm in diameter, glaucous texture producing and color between RHS 4D and RHS 2D with a reddish purple stippling concentrated toward the distal one quarter nearest RHS 60B.

*Pedicel.*—Approximately 2.5 cm long and 3 mm wide, slightly glaucous to slightly lustrous surface, between RHS 76C and RHS 76D with slight lavender tinting if exposed to high sunlight.

*Gynoecium.*—Style — about 6 cm long, 1 mm diameter, near white, lighter than RHS 155D, curled upward at distal end.

*Stigma.*—White, lighter than 155D, 2 to 3 mm diameter.

*Androecium.*—Filaments — six, white lighter than 155D, approximately 1 mm in diameter and to 5 cm long.

*Anthers.*—5 to 6 mm long, 1.5 mm wide, about RHS 83A around margin of abaxial side, white in center, pollen is yellow-orange RHS 17B.

Fruit: Tri-valved dehiscent capsule, about 4.5 cm long and 0.8 cm wide, RHS 158C before drying.

Seeds: Have not yet been observed.

Disease resistance: *Hosta* 'Dancing Stars' shows little susceptibility to slugs compared to other *hosta* and is more resistant to melting out than many other similar cultivars with white leaf centers. It grows best with plenty of moisture but is able to tolerate some drought once mature. Hardiness to at least USDA zone 3, and other disease resistance and susceptibility is typical of *hostas.*

I claim:

1. A new and distinct cultivar of ornamental *Hosta* plant named 'Dancing Stars' having thick substance leaves of deep green margins, light yellow to creamy-white centers and light lavender flowers on cream-colored scapes as herein described and illustrated, suitable as a potted plant, for landscaping specimen or in mass, and for florist type arrangements.

* * * * *